United States Patent [19]

Sack et al.

[11] 4,403,499
[45] Sep. 13, 1983

[54] CABLE TESTER ARRANGEMENT AND METHODS

[76] Inventors: Joel Sack, 45 Beverly Rd., West Orange, N.J. 07052; Irving Neshin, 737 Suburban Rd., Union, N.J. 07083

[21] Appl. No.: 319,253

[22] Filed: Nov. 9, 1981

[51] Int. Cl.³ .............................................. G01N 3/56
[52] U.S. Cl. .......................................... 73/7; 73/158; 73/849
[58] Field of Search ..................... 73/7, 158, 849, 160, 73/794, 812

[56] References Cited

U.S. PATENT DOCUMENTS

| | | | |
|---|---|---|---|
| 443,302 | 12/1890 | Storie | 73/829 |
| 1,168,870 | 1/1916 | Faulkner | 73/158 |
| 2,002,770 | 5/1935 | Field | 73/158 |
| 2,389,912 | 11/1945 | Jacoel | 73/829 |
| 2,435,266 | 2/1948 | Brillhart | 73/158 |
| 2,452,588 | 11/1948 | McFarland | 73/794 |
| 2,557,449 | 6/1951 | Melville | 73/158 |
| 2,910,863 | 11/1959 | Hornbostel et al. | 73/7 |

Primary Examiner—Anthony V. Ciarlante

[57] ABSTRACT

Cable tester and methods of operating the same for subjecting cable such as mining cable to simulated conditions substantially corresponding to actual field conditions as normally encountered by the cable for determining cable longevity, comprising a surface having first and second spaced apart reference points and defining a test drag surface area therebetween, a source adjacent the second point for feed and return of a test span of the cable, first and second moving mechanisms, the first mechanism being connectable to the cable for moving the forward end of the test span from the second to the first point and the second mechanism being connectable to the cable for moving the rearward end of the test span from the second point to the source, and a control system for controlling the first and second mechanisms, for operation in a first test mode for simultaneous reciprocal movement of both mechanisms to drag the test span back and forth along the drag surface area to simulate corresponding field condition dragging, and alternatively for operation in a second test mode for reciprocal movement of at least one said mechanism relative to the other to permit the forming and the removing of a selectively sized loop in the test span on the drag surface area to simulate corresponding field condition looping and unlooping, and optionally including cable flexing a pulley means for reciprocally moving the test span flexibly therethrough to determine cable flexing, e.g. reverse directional flexing, longevity.

13 Claims, 6 Drawing Figures

CABLE TESTER ARRANGEMENT AND METHODS

The present invention relates a cable tester and methods of operating the same, and more particularly to an arrangement and methods for carrying out drag test, loop test and flex test operations, especially for simulating actual field conditions as normally encountered by the cable, for determining corresponding cable longevity.

Various cable testing devices and methods are known. Typical are those set forth in the teachings of U.S. Pat. Nos. 443,302 (Storie), 1,168,870 (Faulkner), 2,002,770 (Field), 2,389,912 (Jacoel), 2,435,266 (Brillhart), 2,452,588 (McFarland), 2,557,449 (Melville), and 3,344,661 (Breuer).

However, these prior art teachings generally only relate to the subjecting of chains or cables to tension to determine their stress or strength limits or the presence of individual bad or weak spots or links therein, or the limits of their electrical characteristics, or in particular to dynamic flexing by passage along a sinuous path in one continuous direction through a series of sheaves (cf. U.S. Pat. No. 2,435,266 to Brillhart), or to static bending or slight torsional twisting (cf. U.S. Pat. No. 2,452,588 to McFarland), or to static flexing in the form of a stationary loop within which a series of sheaves on a common disc are rotated (cf. U.S. Pat. No. 2,557,449).

These prior art teachings do not relate to actual field condition simulation testing devices or methods such as those dealing with the longevity of the cable, such as mining cable, with respect to dragging along a ground surface or looping and unlooping on such a surface, or even to intensive alternate reverse directional flexing.

It is among the objects and advantages of the present invention to overcome the drawbacks and deficiencies of the prior art, and to provide a cable tester and methods of operating the same for simulating actual field conditions as normally encountered by the cable, such as mining cable, and especially electrical cable, for determining corresponding cable longevity, including outer surface wear and inner mechanical and/or electrical integrity, and especially an arrangement and methods for carrying out drag test and loop test operations, and optionally also flex test operations.

It is among the additional objects and advantages of the present invention to provide a cable tester and methods of operating the same of the foregoing type, in which the same overall arrangement permits drag tests and loop tests to be carried out alternatively, and optionally also further alternatively permits flex tests to be carried out, especially alternate reverse directional flexing of the cable in each reciprocal direction of movement through a series of at least two tandem pulleys or sheaves when the cable is moved reciprocally in a forward and then in a return direction through the pulleys.

It is among the further objects and advantages of the present invention to provide a cable tester and methods of operating the same of the foregoing type, which involve an arrangement of simple, durable and inexpensive construction, easily operated at low cost and with minimum workman time and effort for performing drag tests and loop tests, and optionally also flex tests, and which may be converted from a layout for performing one such test to a layout for performing another such test by simply rearranging the cable in the arrangement without the need for physically removing or inserting alternatively usable elements thereat.

Other and further objects and advantages of the present invention will become apparent from a study of the within specification and accompanying drawing, in which:

In accordance with the present invention a cable tester arrangement and methods of operating the same are advantageously provided for subjecting cable such as mining cable and especially electric cable to simulated field conditions substantially corresponding to actual field conditions as normally encountered by the cable for determining cable longevity, including outer surface wear and inner mechanical and/or electrical integrity.

The cable tester arrangement comprises a cable support surface having a first, e.g. adjustable, reference point and a second, e.g. adjustable, reference point spaced apart a selective, e.g. adjustable, distance and defining a test drag surface area therebetween, a source means, such as a guide tube, adjacent the second point for feed and return of a selective, e.g. adjustable, length of a test span of such a cable having a forward cable end portion and a rearward cable end portion, first selectively, e.g. reciprocally, operatable moving means, such as a clutch drive means operated attachment line, operatively connectable to the cable for moving the forward end portion of the test span of the cable from the second point to the first point, and second selectively, e.g. reciprocally, operatable moving means, such as a clutch drive means operated attachment line, operatively connectable to the cable for moving the rearward end portion of the test span of the cable from the second point to the source means, and control means arranged for selectively independently controlling the operation and movement of the first moving means and second moving means.

The control means specifically control the first and second moving means for operating in a first test mode for simultaneous concordant or coordinated reciprocal movement of the first moving means and second moving means to move the test span of the cable relative to the source means and drag the test span back and forth along the drag surface area between the first point and the second point a selective number of times at selective speed and under selective tension to simulate substantially actual field condition dragging as normally encountered by the cable for determining cable dragging longevity, and especially outer surface wear of the cable.

The control means alternatively also specifically control the first and second moving means for operation in a second test mode for reciprocal movement of at least one said moving means relative to the other said moving means to permit the forming of a selectively sized loop in an intermediate section of the test span of the cable on the drag surface area between the first point and the second point in a forward releasing feed phase of reciprocal movement of said at least one moving means, and then the removing of the loop in a rearward selective tension pulling return phase of reciprocal movement of said at least one moving means, a selective number of times to simulate substantially actual field condition looping and unlooping as normally encountered by the cable for determining cable looping and unlooping longevity, and especially the effect of such looping and unlooping on the inner mechanical and/or electrical integrity of the cable.

Cable tension measuring means, such as a tensiometer, are desirably also provided, e.g. at the first moving means, for measuring the tension of the test span of the cable during the particular test.

The source means preferably includes an elongated cable receiving amplitude metering guide or guide tube. Such guide or guide tube may be favorably interposed between the second moving means and the second point.

The first moving means and the second moving means preferably each respectively includes an attachment line connectable to the cable and arranged for feed from and take up onto a reciprocally rotatable reel or drum controlled by the control means.

Thus, the cable tension measuring means may be suitably provided operatively on the attachment line of the first moving means for measuring the tension of the test span of the cable.

Also, the control means may suitably include cam operated amplitude metering linear limit actuation means or trip switch means selectively disposed in the guide or guide tube, and the attachment line of the second moving means may be provided with cooperating cam means and may be arranged for movement along the guide or guide tube to permit the cam means to operate the limit actuation means for correspondingly controlling the operation of the moving means.

According to one preferred feature of the present invention, the first moving means and second moving means are electrically controlled, and the control means includes an energizable circuit for electrically independently controlling the first moving means and the second moving means. Such circuit may for example contain selectively arranged limit switches correspondingly actuated in dependence upon the selected movement amplitude between the first reference point and the second reference point.

Optionally, yet preferably, cable flexing pulley means or sheave means may also be provided adjacent the drag surface area and may be disposed between the first point and the second point, and the control means in turn may be correspondingly arranged for selectively controlling the operation and movement of the first moving means and second moving means for operation in a third test mode for simultaneous reciprocal movement of the first moving means and second moving means to move the test span of the cable, operatively mounted on the pulley means, relative to the source means and flexibly back and forth through the pulley means a selective number of times at selective speed and under selective tension for determining cable flexing longevity, and especially the effect of such flexing on the inner mechanical and/or electrical integrity of the cable.

Significantly, the pulley means includes a series of at least two tandem pulleys or sheaves having corresponding spaced apart, preferably substantially parallel, axes of rotation for tandem alternative reverse directional or sinuous path flexing of the test span of the cable during movement in each reciprocal direction therethrough.

In accordance with the present invention, various alternative methods of using the cable tester arrangement are also advantageously provided.

A first alternative method of using the cable tester arrangement may be employed for carrying out a drag test with a test span of cable having a forward end portion and a rearward end portion. This first method comprises operatively connecting the first moving means to the forward end portion of the test span of the cable and the second moving means to the rearward end portion of the test span of the cable, and reciprocally moving simultaneously the first moving means and second moving means to move the test span of the cable relative to the source means and drag the test span back and forth along the drag surface area between the first point and the second point a selective number of times at selective speed and under selective tension to simulate substantially actual field condition dragging as normally encountered by the cable for determining cable dragging longevity.

A second alternative method of using the cable tester arrangement may be employed for carrying out a loop test with a test span of cable having a forward end portion and a rearward end portion. This second method comprises operatively connecting the first moving means to the forward end portion of the test span of the cable and the second moving means to the rearward end portion of the test span of the cable, and reciprocally moving at least one of said moving means relative to the other said moving means and correspondingly forming a selectively sized loop in an intermediate section of the test span of the cable on the drag surface area between the first point and the second point in a forward releasing feed phase of reciprocal movement of said at least one moving means and a corresponding forward feed phase movement of the cable, and then correspondingly removing the loop in a rearward selective tension pulling return phase of reciprocal movement of said at least one moving means and a corresponding rearward return phase movement of the cable, a selective number of times to simulate substantially actual field condition looping and unlooping as normally encountered by the cable for determining cable looping and unlooping longevity.

A third optional, yet preferred, alternative method of using the cable tester arrangement may be employed for carrying out an alternate reverse directional or sinuous path flex test with a test span of cable having a forward end portion and a rearward end portion. This third optional method comprises operatively connecting the first moving means to the forward end portion of the test span of the cable and the second moving means to the rearward end portion of the test span of the cable, and operatively mounting the test span of the cable on a series of at least two tandem pulleys or sheaves having corresponding spaced apart, preferably substantially parallel, axes of rotation for tandem alternate reverse directional or sinuous path flexing of the test span of the cable during movement in each reciprocal direction therethrough, and reciprocally moving simultaneously the first moving means and second moving means to move the test span of the cable relative to the source means and flexibly back and forth through the tandem pulleys, under tandem alternate reverse directional or sinuous path flexing in each reciprocal direction of movement through the pulleys, a selective number of times at selective speed and under selective tension for determining alternate reverse directional cable flexing longevity.

Figure 1:
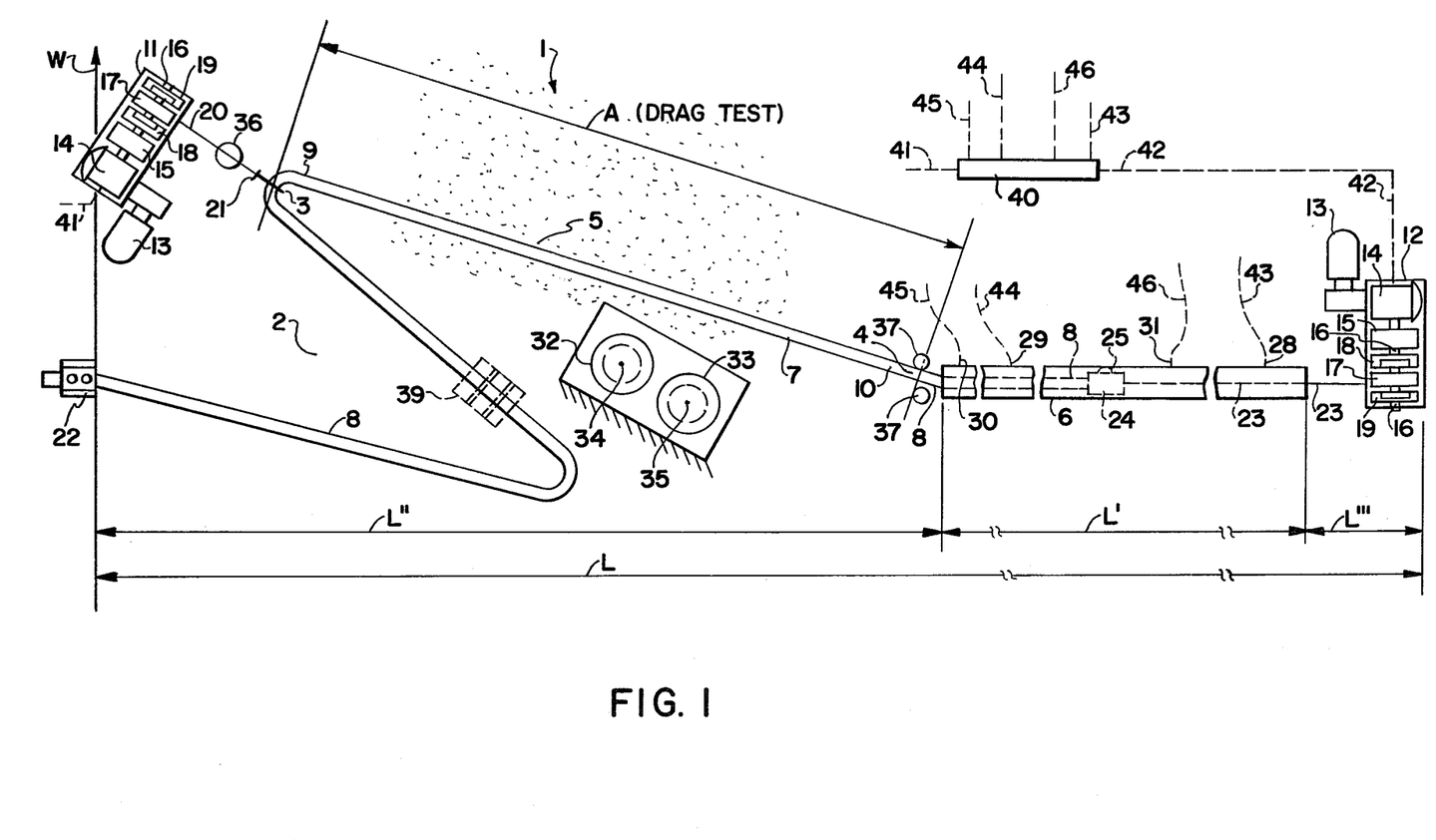
FIG. 1 is a schematic plan view of a cable tester arrangement according to an embodiment of the present invention showing a test span of the cable in a drag test layout between the left and right clutch drives.

Referring to the drawings, and initially to FIG. 1, a cable tester arrangement 1 is shown which contemplates a cable support surface 2 having a first selectively adjustable reference point 3 and a second selectively adjustable reference point 4 spaced apart a selective adjustable distance A and defining a test drag surface area 5 therebetween.

Support surface 2 and drag surface area 5 may be constituted as an actual or naturally occurring dirt or ground formation, such as is found in a mine, or drag surface area 5 of the support surface 2 may instead be formed as a simulated surface substantially corresponding to an actual or naturally occurring dirt or ground formation, such as is found in a mine, and particularly a friction surface having a coefficient of friction substantially equivalent to that of the corresponding actual or naturally occurring dirt or ground formation surface in question.

A source means such as a guide, here shown as an elongated cable receiving amplitude metering guide tube 6, is disposed adjacent the second point 4 for amplitude metered feed and return of a selective adjustable length of a test span 7 of the cable 8 to be tested.

For example, the cable may be a mining cable of the type constituted as a heavy duty electrical cable having an outer protective cured elastomeric jacket thereon, whereby the same may be subjected to simulated field conditions substantially corresponding to actual field conditions as normally encountered by the cable in the mine for determining the corresponding cable longevity thereof, including outer surface wear and inner mechanical and/or electrical integrity.

The test span 7 of the cable 8 has a forward end portion 9 which is first to leave and last to return to the entrance of the guide tube 6, and a rearward end portion 10 which is last to leave and first to return to the entrance of said guide tube.

A first selectively reciprocally operatable moving means and a second selectively reciprocally operatable moving means are provided, here including the left and right opposed first clutch drive 11 and second clutch drive 12 outwardly of the test drag surface area 5. Whereas the first clutch drive 11 is adjacent the first reference point 3, the second clutch drive 12 is remote from the second reference point 4 because the guide tube 6 is conveniently interposed between the second clutch drive 12 and the second reference point 4 for favorable amplitude metered operation.

These clutch drives are preferably duplicates of each other and may be constituted as conventionally controlled electrical drive feed out and take up towing cable or tension line systems of conventional design.

Thus, each of the clutch drives 11 and 12 may correspondingly contain an electric motor 13 coupled by suitable control gearing 14 to a clutch system 15 connected via a drive shaft 16 with a feed out and take up winding drum or reel 17 which is reciprocally rotatably mounted via the drive shaft 16 on the bearings 18 and 19.

The first clutch drive 11 carries an attachment line 20 on its reel 17 which is removably operatively connected to the forward end portion 9 of the test span 7 of the cable 8 via a simple clamp or hook 21 or the like in conventional manner. The reserve slack portion of the cable 8 beyond the hook 21 is suitably anchored in a stationary clamp 22 remote from the drag surface area 5.

The second clutch drive 12, on the other hand, carries an attachment line 23 on its reel 17 which is stationarily operatively connected to the rearward end portion 10 of the test span 7 of the cable 8, e.g. via an end clamp or collar 24 or the like in conventional manner. Collar 24 is slidably disposed in guide tube 6 and provided with a tightening screw or bolt 25 or the like for fixing the cable 8 therein in conventional manner and preferably rigidly so as to prevent any relative axial or rotational movement therebetween.

The attachment line 23 is of course fixedly connected to the collar 24, and the collar 24 may simply be an end ferrule on the end of the cable 8 thereat.

Figure 4:
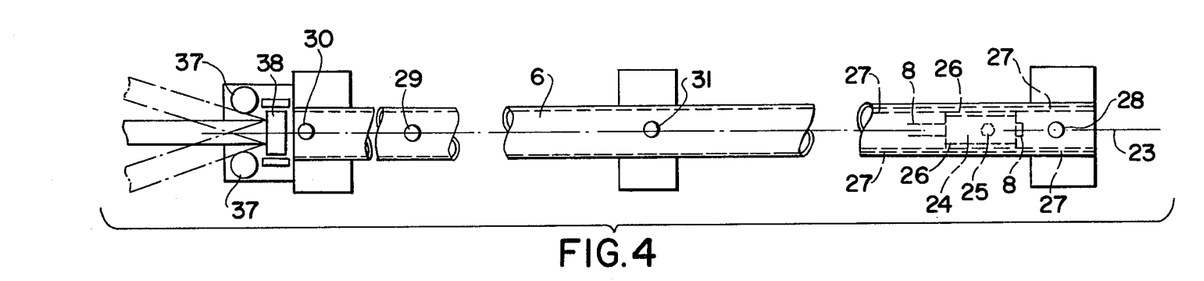
FIG. 4 is a schematic enlarged plan view of the amplitude metering guide tube of the arrangement of FIG. 1 illustrating particular details of construction.
Figure 5:
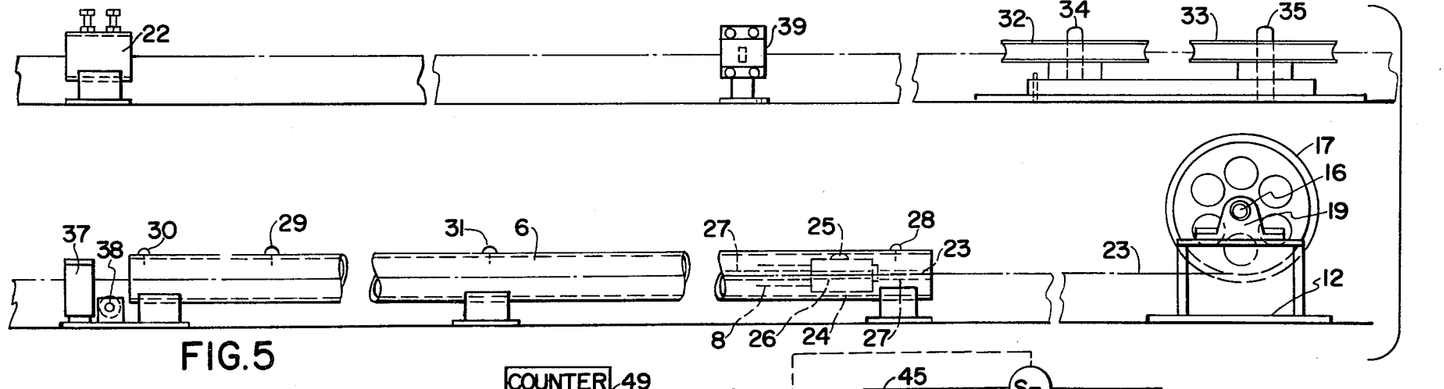
FIG. 5 is a schematic enlarged side view similar to FIG. 4 but generally showing the overall arrangement of FIG. 1 except for the left clutch drive.

More specifically, as shown in phantom in FIGS. 4 and 5, the collar 24 may optionally contain means such as an axially extending and radially outwardly projecting tongue or key 26 on its outer surface on each lateral side for sliding engagement in cooperating means such as a corresponding cooperating side slot or groove 27 optionally provided on each lateral side of the guide tube 6 and extending the length of the interior of the guide tube. In this way, while the collar 24 and the cable 8 connected thereto are free to move together reciprocally back and forth along the smooth interior of the guide tube 6, the collar 24 is prevented from rotating relative to the guide tube, and the cable 8 when rigidly fixed by the bolt 25 to the collar 24 is prevented not only from rotating relative to the collar but also from rotating relative to the guide tube 6.

Nevertheless, where it is not desired or essential to prevent relative rotational movement between the collar 24 and the guide tube 6, the keys 26 and the grooves 27 or equivalent means thereto may be omitted, yet in any case sufficient clearance between the interior of the guide tube 6 and the adjacent portions of the collar 24 and bolt 25 must be provided to permit the collar 24 to reciprocate along the extent of the guide tube, as the artisan will appreciate.

Thus, the first clutch drive 11 is operatively connectable via the attachment line 20 and hook 21 to the cable 8 for moving the forward end portion 9 of the test span 7 from the second reference point 4 to the first reference point 3, while the second clutch drive 12 is operatively connectable via the attachment line 23 and the collar 24 to the cable 8 for moving the rearward end portion 10 of the test span 7 from the second reference point 4 to the guide tube 6.

To effectuate and coordinate such movement, suitable control means are provided. Such control means are arranged for selectively independently controlling in conventional manner the operation and movement of the first clutch drive 11 and of the second clutch drive 12 and in turn of the reels 17 and attachment lines 20 and 23. The control means suitably include cam operated amplitude metering linear limit actuation means or trip switch means selectively disposed in the guide tube 6, here shown in the form of conventional limit switches 28, 29, 30 and 31.

Appropriately, the attachment line 23 of the second clutch drive 12 may suitably include cooperating cam means and be arranged for movement along the guide tube 6 to permit the cam means to operate the limit actuation means, e.g. limit switches 28, 29, 30 and 31 as the case may be, for correspondingly controlling the operation of the first clutch drive 11 and the second clutch drive 12.

Advantageously, as shown more clearly in FIGS. 4 and 5, the cam means may be simply provided by utilizing thereas the bolt 25 on the collar 24 which rides back and forth within the interior of the guide tube 6, and accordingly by mounting the limit switches 28, 29, 30 and 31 to project into the interior of the guide tube 6 and across the movement path of the bolt 25 along the linear extent of the guide tube.

Nevertheless, where the collar 24 is merely an end ferrule on the cable 8 which does not contain any said bolt 25, the attachment line 23 may be provided with a counterpart radially extending finger or the like serving the same purpose as bolt 25, i.e. as a cooperating cam means arranged for movement along the guide tube 6 to operate the amplitude metering limit actuation means.

The various limit switches 28, 39, 30 and 31, or other cam operated amplitude metering linear limit actuation means may be operatively connected in any suitable conventional manner for controlling the operation and movement of the clutch drives 11 and 12 and in turn of the reels 17 and attachment lines 20 and 23.

For example, such operative connection may include conventionally interposed servomotor means or other control interconnecting means (not shown) for operating the clutch drives 11 and 12 in the usual manner to start, stop and reverse the direction of rotation, as well as select the speed of movement, of the respective reels 17 independently of each other.

According to a favorable feature of the present invention, the motors 13 of the clutch drives are conveniently provided as electrically controlled motors, e.g. heavy duty electrical motors, which may be reversible motors, and the control means includes an energizable circuit for electrically independently controlling the gear shifting operation of these motors as may be seen from FIG. 6 more fully described hereinbelow, e.g. to change speed and direction of rotation as well as to start and stop rotational operation of the shafts 16.

This circuit advantageously may contain the selectively arranged limit switches 28, 29, 30 and 31 so as to be correspondingly actuated in dependence upon the selective adjustable movement amplitude or distance between the first reference point 3 and the second reference point 4, depending upon the type of test being carried out.

Optionally, yet preferably, cable flexing pulley means or sheave means may be provided adjacent the drag surface area 5 and disposed between the first reference point 3 and the second reference point 4. Preferably, the pulley means or sheave means includes a series of at least two tandem pulleys or sheaves 32 and 33, having corresponding spaced apart and preferably substantially parallel, axes of rotation 34 and 35. This arrangement permits tandem alternate reverse directional or sinuous path flexing of the test span 7 of the cable 8 during movement in each reciprocal direction therethrough.

Cable tension measuring means such as a tensiometer 36 is desirably provided, preferably at the first clutch drive 11, for measuring the tension of the test span 7 of the cable 8 during each particular test. The tensiometer 36 may thus be suitably mounted in conventional manner on the attachment line 20 of the first clutch drive 11.

At the opposite end of the drag surface area 5 from that where the tensiometer 36 and hook 21 are located, the guide tube 6 is desirably provided with a pair of vertical guide rollers 37 and a bottom horizontal guide roller 38 at its entrance (see FIGS. 4 and 5). Together these elements insure the positioning of the cable 8 on or close to the support surface 2, depending on the test being carried out, as well as the guiding and proper movement and holding of the test span 7 of the cable 8 relative to the drag surface area 5 and the first and second reference points 3 and 4.

Nevertheless, an optional randomly positionable auxiliary guide 39 (see FIG. 5) may be provided for selectively guiding any desired intermediate portion of the cable 8 during any particular test. Thus, auxiliary guide 39, as shown in phantom in FIG. 1, for instance, may be used to guide the reserve excess portion of the cable 8 situated beyond the hook 21. Auxiliary guide 39 may contain opposed vertical rollers and a bottom horizontal roller similar to the arrangment of rollers 37 and 38 at the entrance of the guide tube 6 for facilitating the positioning and guidance therethrough of the portion of the cable 8 carried thereby.

According to the drag test layout shown in FIG. 1, the control means specifically control the first and second clutch drives 11 and 12 for operation in a first test mode for simultaneous coordinated reciprocal movement of the reels 17 and in turn of the attachment lines 20 and 23 and of the hook 21 and the collar 24 so as to move the test span 7 relative to the guide tube 6 and drag the dead weight test span back and forth along the drag surface area 5 between the first point 3 and the second point 4 a selective number of times at selective speed and under selective tension as measured by the tensiometer 36.

This will simulate substantially actual field condition dragging of the dead weight of the cable, as normally encountered by the cable, and may be used for determining the cable dragging longevity thereof, and especially the extent to which the outer protective jacket on such a cable withstands the wearing friction of the surface of the test drag surface area 5 across which the test span is dragged. The test result may be readily evaluated by visual inspection and by the usual procedures appropriate thereto.

As the artisan will appreciate, the amplitude of dragging movement between the first point 3 and the second point 4 may be selectively adjusted as desired, just as the speed of movement and the number of times the test span is dragged back and forth, whereby to provide standardized dragging surfaces and amplitudes and standardized speeds of movement and numbers of times that the test span is dragged back and forth. Also, the drag test may be carried out for an arbitrary minimum number of times or until apparent failure of the jacket.

This type of drag test layout is suitably equivalent to an actual mine cable layout in a mine wherein the cable is supplied from a supply reel on a set up similar to that of the second clutch drive 12 and guided by a clutch drive similar to the first clutch drive 11 spaced from the supply reel a distance analogous to that contemplated in FIG. 1, for serving a randomly moving mine vehicle or the like at a point along the cable corresponding to that of the stationary clamp 22, and which may be optionally also provided with an auxiliary guide similar to auxiliary guide 39.

Such actual mine cable layout permits the randomly moving mine vehicle to move without hindrance in a manner well supplied with increasing or decreasing intermediate lengths of immediately available cable and whose range and functioning are thereby enhanced, yet this random movement subjects the cable to dragging wear of the type contemplated in the instant drag test layout.

Figure 2:
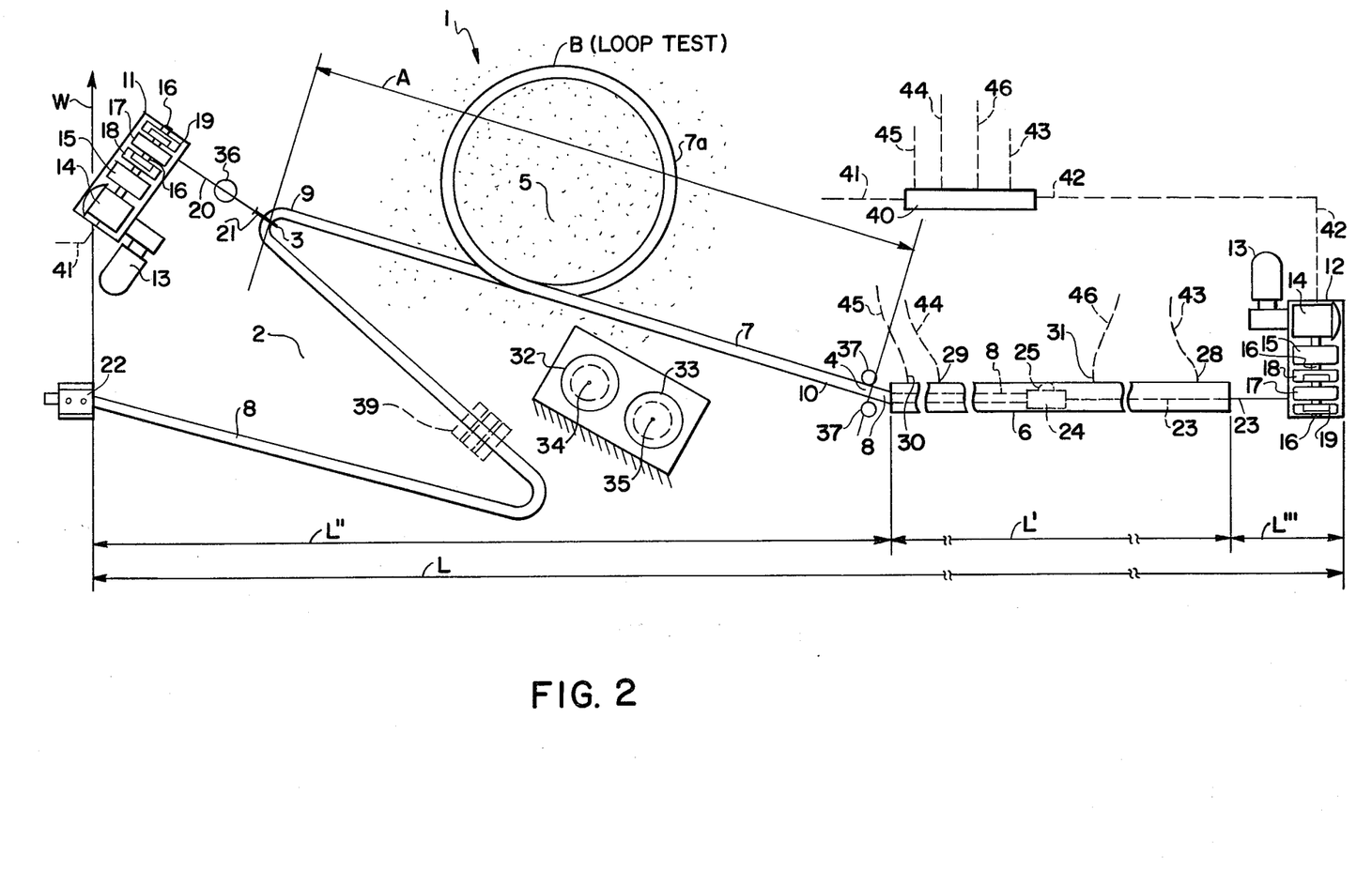
FIG. 2 is a schematic plan view of the arrangement of FIG. 1 showing the test span of the cable in a corresponding loop test layout in which the loop in the cable is exaggerated for clarity of illustration.

According to the loop test layout shown in FIG. 2, the control means in the very same apparatus at that of FIG. 1 alternatively also specifically control the first and second clutch drives 11 and 12 for operation in a second test mode, in a first case, for reciprocal movement only of the reel 17, attachment line 23 and collar 24 of the second clutch drive 12 while the first clutch drive 11 remains stationary or inoperative once the hook 21 and the forward end portion 9 of the cable 8 are positioned at the first reference point 3.

This reciprocal operation only of the second clutch drive 12, according to said first case loop test, permits the forming of a selectively sized loop 7a in an intermediate section of the test span 7 on the drag surface area 7 between the first point 3 and the second point 4 in a forward releasing feed phase of reciprocal movement of the reel 17, attachment line 23 and collar 24. During this feeding time, a workman is able to loop the increasingly slackening test span 7 upon itself to provide the loop 7a in an intermediate section thereof and form the loop into a size limited by the selective amplitude of outward movement of the cable 8 from the guide tube 6.

It will be appreciated that since the attachment line 23 is being continuously released, the workman need only pull concordantly on the test span 7 whereby the collar 24 will increasingly move outwardly along the guide tube 6 and the cable will ride correspondingly outwardly on the collar 24 and be guided by the rollers 37 and 38 to achieve the desired loop diameter size with little effort. The interior of the guide tube 6 is of course suitably smooth to facilitate movement of the cable 8 therealong.

Once the outward movement and loop formation have been accomplished, the counterpart reciprocal operation of the second clutch drive 12 permits the removal of the loop 7a, resting on the drag surface area 5, in a rearward selective tension pulling return phase of reciprocal movement of the reel 17, attachment line 23 and collar 24.

This loop forming and loop removing operation may be carried out a selective number of times and under selective tension during the loop removing phase as measured by the tensiometer 36.

This operation will likewise simulate substantially actual field condition looping and unlooping of the dead weight cable resting on the drag surface area 5, as normally encountered by the cable. It may be used for determining the cable looping and unlooping longevity thereof, and especially the effect of such looping and unlooping on the inner mechanical and/or electrical integrity of the cable.

As the artisan will appreciate, according to said first case loop test, the amplitude of movement of the reel 17, attachment line 23 and collar 24 and in turn the size of the loop 7a as well as its location along the intermediate section of the test span 7, may be adjusted as desired, just as the number of times the loop is formed to test size and pulled until the loop is completely removed. In this way, a standardized loop size may be tested for inherent tortional twisting a standardized number of times.

Nevertheless, the looping and unlooping may be carried out without controlled torsional twisting, as where the collar 24 is free to rotate relative to the interior of the guide tube 6, or even where the cable 8 is mounted optionally on the collar 24 in a manner permitting the cable to rotate relative to the collar 24. In such instance, the pull on the cable 8 during the rearward tension pulling return phase of reciprocal movement of the reel 17, attachment 23 and collar 24 will relieve rather than propagate or distribute the torsional stress set up initially in the cable 8 upon the forming of the loop 7a therein.

Preferably, however, such tortional twisting is suitably retained and controlled, as where the collar 24 contains keys 26 and the guide tube 6 contains cooperating grooves 27 therefor to prevent rotation therebetween, and in turn where the cable 8 is fixed by the bolt 25 or the like to the collar 24 likewise to prevent any rotation of the cable 8. In this instance, the pull on the cable during the rearward tension pulling return phase of reciprocal movement of the reel 17, attachment line 23 and collar 24 will propagate and distribute along its length the torsional stress initially set up in the cable 8 upon the forming of the loop 7a therein for more closely simulating actual field conditions.

This type of loop test layout is suitably equivalent to the actual mine cable layout discussed earlier in connection with the drag test layout in FIG. 1. In such actual mine cable layout, the cable frequently is subjected to random looping and unlooping in the area thereof corresponding to the drag surface area 5, i.e. in a manner substantially equivalent to the instant loop test.

Alternatively, as noted more fully hereinafter, in a second case the loop test may be carried out in random manner such that only the reel 17 and attachment line 20 of the first clutch drive 11 are reciprocally moved while the second clutch drive 12 remains stationary or inoperative, whereas in a third case the loop test may be carried out in random manner such that both the first clutch drive 11 and the second clutch drive 12 are used to permit the forming and the removing of the loop 7a.

Figure 3:
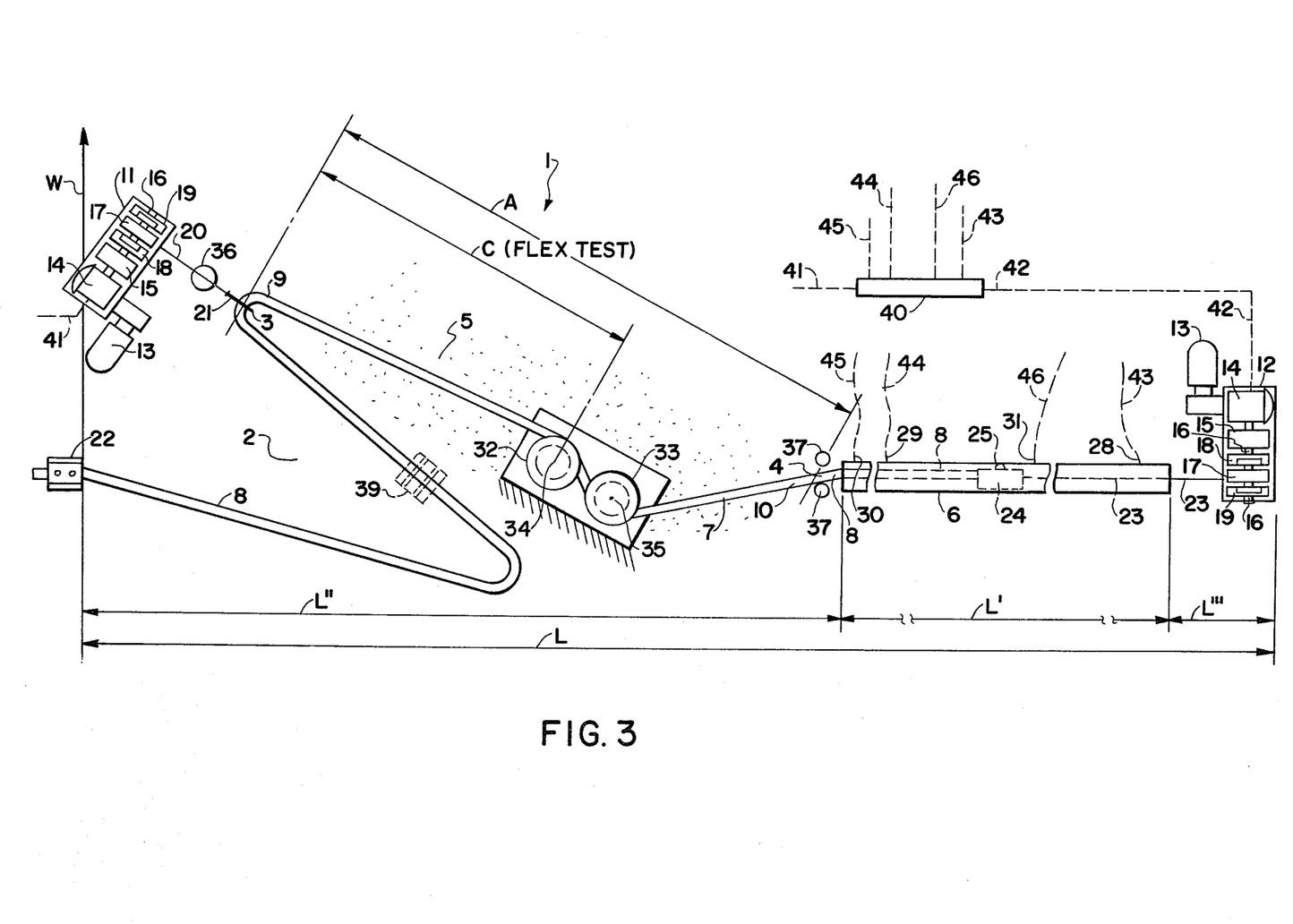
FIG. 3 is a schematic plan view of the arrangement of FIG. 1 showing the test span of the cable in a corresponding flex test layout.

According to the flex test layout shown in FIG. 3, the control means in the very same apparatus as that of FIG. 1 and FIG. 2 may optionally alternatively also specifically control the first and second clutch drives 11 and 12 for operation in a third test mode for simultaneous reciprocal movement of the reels 17 and in turn of the attachment lines 20 and 23 and of the hook 21 and the collar 24 so as to move the test span 7, operatively mounted on the tandem pulleys 32 and 33, relative to the guide tube 6 and flexibly back and forth through the pulleys a selective number of times at selective speed and under selective tension as measured by the tensiometer 36.

This may be effectively used for determining cable flexing longevity, and especially the effect on the inner mechanical and/or electrical integrity of the cable of such tandem alternate reverse directional or sinuous path flexing of the cable, i.e. during movement in each reciprocal direction therethrough.

Thus, this flex test does not merely subject the cable to unilateral passage through a series of pulleys for tandem alternate reverse directional or sinuous path flexing, but rather subjects the very same test span of the cable firstly to tandem alternate reverse directional or sinuous path flexing during movement in a forward direction through the series of pulleys, and secondly to tandem alternate reverse directional or sinuous path flexing during reverse or opposite movement in a rearward direction through the same series of pulleys, repeated a selectively significant number of times.

As the artisan will appreciate, the amplitude of movement relatively between the first point 3 and the second point 4 may be adjusted as desired, just as the number of times the test span is passed in each respective direction through the series of pulleys, whereby to provide standardized flexing amplitudes and standardized numbers of flexing times for an inherently intensive flex test.

This type of flex test layout is readily accommodated by the arrangement of FIG. 1 since it utilizes the same apparatus and operating procedures as the drag test for the fact that the cable is mounted on the tandem pulleys 32 and 33 rather than dragged along the drag surface area 5. Of course, the pulleys 32 and 33 are suitably laterally offset from the path of the cable when the drag test and the loop test are otherwise carried out, yet such pulleys are conveniently accessible for carrying out the flex test.

This flex test is also distinguished by the fact that the intensive repeated flexing may be carried out rapidly in dependence upon the peripheral rotational speed of the reels 17 and the interval between the end of one phase of reciprocal movement and the start of the opposite phase of reciprocal movement.

Of course, by mounting the pulleys 32 and 33 on the support surface 2 displaceably, i.e. about pivot axis 35, the pulley 34 may be moved clockwise a selective distance, i.e. upwardly and to the right from the position shown in FIG. 3, when the flex test layout is used, thereby providing a tandem pulley orientation with respect to the attachment line 20 and the guide tube 6 for more pronounced sinuous curvature flexing of the test span 7.

In order to control the various operations of the tests, as shown in FIGS. 1, 2 and 3, a control console 40 is provided, preferably adjacent to and in full view of the drag surface area 5. The electric motor 13 and control gearing 14 of the first clutch drive 11 are operatively connected via the first conductor 41 with the control console 40, and correspondingly the electric motor 13 and control gearing 14 of the second clutch drive 12 are also operatively connected via the second conductor 42 with the control console 40. Likewise, the limit switches 28, 29, 30 and 31 are appropriately connected to the control console 40 by the respective conductors 43, 44, 45 and 46.

An operator at the console 40 may therefore control in conventional manner the starting, stopping and reversing of the movement, as well as the rotational speed, of each reel 17 independently of the other, or their simultaneous starting, stopping and reversing of movement, as well as their rotational speed, in conjoint coordinated manner, using conventional controlling and controlled elements for this purpose.

Figure 6:
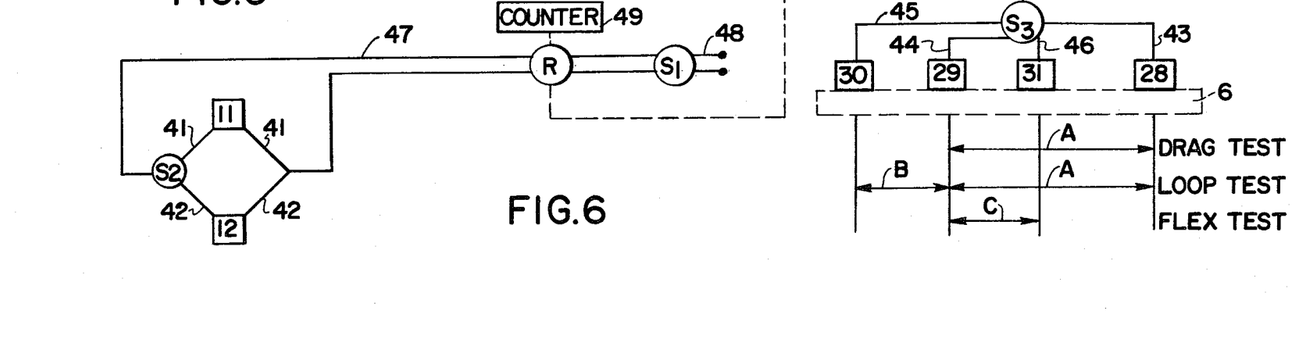
FIG. 6 is a schematic diagram showing an embodiment of the control means for operating the left and right clutch drives and for changing the corresponding amplitudes of movement of the test span in connection with alternative drag, loop and flex tests.

As may be seen in FIG. 6, a control circuit 47 is provided in console 40, which is energizable by an appropriate current source 48, and which contains an on-off main switch $S_1$ as well as both motors 13 and control gearing 14 of both clutch drives 11 and 12 via the corresponding first conductor 41 and the second conductor 42.

If desired, the switch $S_2$ may be provided as a multiple position switch which in a first position closes the connection with the first conductor 41 to control the operation and movement of the first clutch drive 11 and opens simultaneously the connection with the second conductor 42 to exclude the second clutch drive 12, for operating only the first clutch drive 11.

In a second position of the switch $S_2$, it closes the connection with the second conductor 42 to control the operation and movement of the second clutch drive 12 and simultaneously opens the connection with the first conductor 41 to exclude the first clutch drive, for operating only the second clutch drive 12.

In a combination third position of the switch $S_2$, it closes the connection with both the first conductor 41 and the second conductor 42 to control the operation and movement of each clutch drive, for operating both the first clutch drive 11 and the second clutch drive 12 simultaneously and concordantly, e.g. in the same or opposite functional rotational directions.

On the other hand, switch $S_2$ may in fact represent two individual switches arranged to accomplish the independent energizing control of the operation and movement in one or the other functional rotational direction of each of the clutch drives respectively, so that when both switches are actuated together both clutch drives are controlled for concordant operation and movement, and so that when only one switch is actuated only the one clutch drive associated therewith is operated and in turn controlled while the other clutch drive is excluded from operation.

If desired, the control circuit 47 may also be provided with a relay R or the like of the conventional type for controlling the starting, stopping and reversing of direction of rotation of the reels 17 in conjunction with the operation of the limit switches 28, 29, 30 and 31.

A suitable counter 49 may be operatively connected in conventional manner to the system, e.g. to the relay R, to count each changeover of such direction of rotation and thus of the number of individual back and forth movements of one or both of the reels 17 and in turn of the cable 8, or to count only the return cycle movements corresponding to the return movement of the cable 8 back into the guide tube 6.

Moreover, limit switch 28 may be positioned at the remotest point on the guide tube 6 from the second reference point 4, and the limit switch 29 may be positioned at an intermediate proximate point on the guide tube 6. The limit switch 28 is operatively connected via the conductor 43 to the circuit 47 and the limit switch 29 is correspondingly operatively connected via the conductor 44 to the circuit 47, with both switches being arranged in conventional manner so as to control the operation of the relay R for controlling in turn the operation and movement of the clutch drives 11 and 12.

In this way, for example, when the reel 17 of the first clutch drive 11 is energized to move the cable 8 outwardly from the guide tube 6 to move in turn the forward end portion 9 to the cable 8 from the second reference point 4 to the first reference point 3, the bolt 25 will trip the limit switch 29 at the end of the forward movement, causing the relay R to reverse the operation. Normally, during this time the reel 17 of the second clutch drive 12 is also energized in unison therewith to feed out the attachment line 23 in concordant manner.

Upon such reversal, the reel 17 of the second clutch drive 12 is energized to move the rearward end portion 10 of the cable 8 from the second reference point 4 inwardly into the guide tube 6 once more and in turn the forward end portion 9 is moved back to the second reference point 4. Likewise, during this time the reel 17 of the first clutch drive 11 is also normally energized in unison therewith to feed out the attachment line 20 in concordant manner. At the end of this rearward movement, the bolt 24 will trip the limit switch 28, causing the relay R to reverse the operation once more for repeating the reciprocal operation cycle, with appropriate counting via the counter 49.

Understandably, the linear distance between the limit switch 28 and the limit switch 29 will correspond to the linear distance between the second reference point 4 and the first reference point 3, e.g. as used in the drag test of FIG. 1. This is also used in the loop test of FIG. 2 to position preliminarily the forward end portion 9 of the test span 7 at the first reference point 3, i.e. prior to further outward movement of the cable 8 to the limit switch 30 which is at the closest point on the guide tube 6 to the second reference point 4, as will be described more fully hereinafter.

In the case of the flex test, however, e.g. as used in the layout of FIG. 3, since the maximum distance between the first reference point 3, i.e. adjacent the first clutch drive 11, and the nearest pulley 32 is less than the full amplitude between the first reference point 3 and the second reference point 4 adjacent the rollers 37 at the entrance of the guide tube 6, the limit switch 31 instead of the limit switch 28 is used with the limit switch 29.

The shorter linear distance between the limit switch 29 and the limit switch 31 will correspond to the shorter linear distance between the nearest pulley 32 and the first reference point 3 for the reciprocal amplitude used in the flex test. Limit switch 31 is positioned at an intermediate distal point on the guide tube 6, i.e. between the remotest point at which limit switch 28 is located and the intermediate proximate point at which limit switch 29 is located.

To achieve changeover from the drag test layout to the flex test layout, the switch $S_3$ may be desirably provided for disconnecting the conductor 43 and the limit switch 28 from the relay R and in turn operatively connecting the conductor 46 and the limit switch 31 with the relay R. Thus, the operator at the console 40 may change the amplitude from that for the drag test to that for the flex test, and vice versa, by operating the changeover switch $S_3$.

The switch $S_3$ may be a multiple position switch of conventional design, and may also be used to achieve changeover to the loop test layout from the drag test layout, by disconnecting the conductor 43 and the limit switch 28 from the relay R and in turn operatively connecting the conductor 45 and the limit switch 30 with the relay R for conjoint use with the limit switch 29. This takes place after the preliminary positioning of the forward end portion 9 of the test span at the first reference point 3 as described above.

On the other hand, switch $S_3$ may in fact represent a series of three individual switches arranged to accomplish the independent selective switching in exclusively of specific pairs of the limit switches. Thus, the limit switches 28 and 29 may be actuated by a first switch or drag test switch for achieving an amplitude of reciprocal movement of the cable 8 corresponding to the distance A between the second reference point 4 and the first reference point 3 (cf. FIG. 1) at when the forward end portion 9 of the test span 7 is moved back and forth between the second reference point 4 and the first reference point 3 in the drag test. This actuation excludes the other limit switches from operation.

Also, the limit switches 31 and 29 may be actuated by a second switch or flex test switch, i.e. corresponding to such switch $S_3$, for achieving an amplitude of reciprocal movement of the cable 8 corresponding to the distance C between the pulley 32 and the first reference point 3 (see FIG. 3), as when the forward end portion 9 of the test span 7 is moved back and forth between the pulley 32 and the first reference point 3 in the flex test. This actuation likewise excludes the other limit switches from operation.

It will be appreciated in this regard that because of the presence of the hook 21, the maximum movement of the cable 8 through the pulleys 32 and 33 in the direction of the guide tube 6 will be limited by the hook 21. Otherwise, the hook 21 will engage the pulley 32, which might not only disturb the test but more importantly cause damage to the hook and pulley and even extraneous damage to the cable itself.

It should also be noted in this regard that because of the offset positioning of the pulleys 32 and 33 relative to the straight line normal disposition of the cable between the rollers 37 at the entrance to the guide tube 6 and the forward end portion 9 of the test span 7 when at the first reference point 3, where the cable 8 is mounted over the pulleys, and especially in the case where the pulley 32 is displaceable, e.g. clockwise about the axis 35 of the pulley 33, in an upward direction to the right, i.e. towards the guide tube 6, as viewed in FIG. 3, whereby to provide an increased circular sinous path approaching more completely a closed figure eight configuration than that shown in FIG. 3, an additional length of the cable 8 must be utilized in the case of the flex test beyond that used in the case of the drag test.

Such additional length may be readily provided by simply moving through the hook 21 an additional portion of the reverse length of the cable 8 normally positioned between the hook 21 and the stationary clamp 22. Such additional portion may be returned to the other side of the hook 21 after the flex test has been completed.

Otherwise, such additional length would have to be contributed by moving a further corresponding length of the cable 8 outwardly from the guide tube 6. This would in turn necessitate the inclusion of a fifth limit switch on the guide tube 6 in place of the limit switch 29 to demark the position of the cable 8 corresponding to that of the forward end portion 9 of the cable when at the first reference point 3. It will also necessitate the readjustment of the limit switch 31 to a position consistent with such fifth limit switch and corresponding to that of the forward end portion 9 when at the pulley 32. In this case, the second switch or flex test switch, i.e. corresponding to the switch $S_3$, will actuate the limit switch 31 and the fifth limit switch, and will in turn exclude the other limit switches from operation.

Lastly, the limit switches 29 and 30 may be actuated by a third switch or loop test switch, i.e. corresponding to such switch $S_3$, for achieving, in the first case loop test, an amplitude of reciprocal movement of cable 8 corresponding to the distance B defined by the circumference of the intermediate section of the test span 7 looped upon itself in forming the selectively sized loop 7a (see FIG. 2) in the forward releasing feed phase of reciprocal movement of the second clutch drive 12, i.e. after the forward end portion 9 of the test span 7 has been moved from the second reference point 4 to the first reference point 3 in a preliminary single phase movement corresponding to that of the drag test. This actuation similarly excludes the other limit switches from operation.

Thus, prior to actuation of said third switch or loop test switch, the first said switch or drag test switch must be actuated to include only the limit switches 28 and 29 to permit the forward end portion 9 of the test span 7 to be moved to the first reference point 3 for such preliminary positioning as aforesaid.

Of course, when the third switch or loop test switch is thereafter actuated, the switch $S_2$ will also be actuated to exclude the first clutch drive 11 from operation and limit operation and control to the second clutch drive 12 alone.

It will be appreciated that in the first case loop test the removing of the loop 7a in the rearward tension pulling return phase of reciprocal movement of the second clutch drive 12, while the first clutch drive 11 remains stationary or inoperative, requires the full length of the test span 7 to be made taut. The amplitude of movement of the cable 8 back into the guide tube 6 to achieve such taut condition and which corresponds to the circumference of the loop 7a, is demarked by the distance between the limit switch 30 and the limit switch 29 on the guide tube 6.

When the latter operation is completed, the limit switch 29 will be tripped, causing the forward releasing feed phase of reciprocal movement of the second clutch drive 12 to be repeated. During this feeding time, the workman can pull the cable 8 increasingly from the guide tube 6 to form the loop 7a once again. Of course, the size of the loop 7a is determined by the tripping of the limit switch 30 which stops further outward feed of the cable 8 from the guide tube 6.

Whether or not a multiple position switch $S_3$ is provided, or three individual switches akin thereto, i.e. a drag test switch, a flex test switch and a loop test switch, a suitable counter 49 will normally be provided in the control circuit in conventional manner to record the number of individual back and forth movements or the number of repeated cycles for each type test, e.g. in response to the tripping of the appropriate limit switch.

Moreover, if desired, the same two switches may be used for all of the tests, e.g. limit switches 28 and 29, by merely removably repositioning them at selective points along the guide tube 6 corresponding to the concordant amplitude of movement of the cable 8 desired for each particular test or type of test, in which event the limit switches 30 and 31 may be omitted. These two switches 28 and 29 may be so positioned stationarily yet removably through insert apertures or the like (not shown) in the guide tube 6 at predetermined points therealong corresponding to the points at which the four switches 28, 29, 30 and 31 would otherwise be positioned.

In this event, the switch $S_3$ may be omitted also, to provide a simple selectively adjustable length amplitude between the limit switches 28 and 29 as maximum and minimum limit switches, e.g. connected to the circuit 47 via the relay R, for controlling the starting, stopping and reversing of the operation and movement of the first clutch drive 11 and the second clutch drive 12, and more particularly of the reels 17 thereof, all in full view of the operator at control console 40.

Naturally, the length of the guide tube 6 will depend upon the maximum amplitude of movement of the cable 8 to be accommodated. This is determined in turn by the distance A for the drag test, the combined distances A and B for the first case loop test, and the intermediate distance C for the flex test, as shown in FIGS. 1,2,3 and also in FIG. 6 in specific relationship to the positioning of the limit switches 30, 29, 31 and 28.

Additionally, the two clutch drives may be operatively mechanically connected with the control console 40, so that upon tripping of a particular limit switch, the operator can merely individually mechanically reverse the operation of the reel or reels 17 for rotation in the opposite direction and conventionally adjust the speed of movement desired. If the limit switch serves to deactivate or stop the operation of the clutch drive or drives in this kind of arrangement, then the operator can individually mechanically reverse and reactivate or restart such operation and reset the limit switch.

Of course, it is generally possible to use any appropriate type of reversible motor or drive means and control circuit arrangement for effecting the desired back and forth reversible rotation of the individual reels 17 thereof as contemplated herein.

The overall length L of the test layout area may be roughly about 35 feet and the overall width W thereof embracive of the area where the loop 7a is formed as well as the area containing the pulleys 32 and 33 may be roughly about 10 to 12 feet. In this regard, for example, the guide tube 6 may have a length L' of about 12 feet, and the main test area may have a length L" of about 19 feet, so that correspondingly the offside area where the second clutch drive 12 is situated will have a remainder length L'" of about 4 feet.

This comprehensive test layout thus is able more or less to duplicate an actual working area where the cable to be tested is normally used, e.g. in a mine. Hence, the tests performed will simulate as closely as possible the service conditions under which the cable being tested will be utilized in practice, for obtaining more valid as well as more reliable test results, especially with regard to the drag test and the loop test. In fact, the cable tester arrangement 1 can be actually set up in an existing mine itself for essentially authentic environment testing of the cable.

Generally, as the artisan will appreciate, any conventional control means may be used for controlling the operation and movement of the first and second moving means so as to achieve the corresponding movement as contemplated herein.

Of course, considering the amplitude metering purpose of the guide tube 6, any other appropriate source means may be utilized in place thereof, e.g. adjacent the second reference point, for achieving such purpose in accordance with the broad aspects of the present invention.

Moreover, as noted earlier, alternatively the loop test can be conducted in random manner in a second case using the first clutch drive 11 alone while the second clutch drive 12 remains stationary or inoperative, whereupon the limit switch 30 can be omitted. Hence, the operator can use suitable switch means and control means in conventional manner to operate the reel 17 of the first clutch drive 11 to release the attachment line 20 so that the workman can pull on the cable and form a random loop therein. Then, the reel 17 can be stopped and operated in the reverse direction to take up the attachment line 20 to remove the random loop and place the unlooped cable under the full torque or load of the reel.

The corresponding tension developed thereby in the second case loop test can be measured by the tensionmeter 36 in the same way as in the first loop test, i.e. where the second clutch drive 12 is used alone to perform the loop test.

The size of the loop 7a and its location in the intermediate section of the test span 7 can be standardized in the second case loop test nevertheless, by marking off a length therealong corresponding to the loop circumference desired, i.e. distance C. In this event, the second case loop test will not be a random loop test to the extent that the loop 7a will be formed each time of the same circumference and at the same location in the cable because of the use of a marked off length for this purpose.

At the same time, as aforesaid, this procedure in the second case loop test avoids the need for the limit switch 30, and instead the operator directly controls the starting, stopping and reverse operation for forming and removing the loop 7a by use of appropriate switch means and control means arranged in conventional manner while visually observing the loop forming and loop removing operation from the control console 40.

Additionally, as noted earlier, alternatively the loop test can be conducted in random manner in a third case using the first clutch drive 11 and the second clutch drive 12 together, whereupon the limit switch 30 can likewise be omitted. In this instance also, the operator can use suitable switching means and control means in conventional manner to operate both reels 17 to release the corresponding attachment lines 20 and 23 at the same time so that the workman can pull on the cable 8 from both end directions of the test span 7 and form a random loop therein.

Then, both reels 17 can be stopped and operated in the reverse direction to take up the corresponding attachment lines 20 and 23 once more to remove the random loop. In this third case loop test, the resulting unlooped cable will be placed under the full cumulative opposing torques or loads of both oppositely moving reels. Here also, the corresponding resultant tension developed thereby on the thusly unlooped cable in the third case loop test can be measured by the tensiometer 36 in the same way as in the first case and second case loop tests.

The size of the loop 7a and its location in the intermediate section of the test span 7 can be standardized in the third case loop test by likewise marking off a length therealong corresponding to the loop circumference desired, i.e. distance C, to the same effect as noted above for the second case loop test. The operator in the third case loop test also directly controls the operation in similar manner and by like means as in the second case loop test, but of course in this instance the reels 17 will move in functionally opposite directions for conjoint feeding release and for conjoint pulling return of the cable 8.

In review, the cable tester arrangement 1 may be used for carrying our a drag test with the layout of FIG. 1, a loop test with the layout of FIG. 2, and a flex test with the layout of FIG. 3. In all tests, of course, the first clutch drive 11 must be operatively connected to the forward end portion 9 of the test span 7 of the cable 8 and the second clutch drive 12 must be operatively connected to the rearward end portion 10 of the test span of the cable for proper guiding and control of the cable 8.

The drag test entails reciprocally moving simultaneously, e.g. concordantly synchronously, at selective speed the first clutch drive 11 and the second clutch drive 12, and specifically the reels 17 thereof, so as to move the test span 7 relative to the guide tube 6 and drag the test span back and forth along the drag surface area 5 between the first reference point 3 and the second reference point 4, i.e. at a movement amplitude corresponding to the linear distance A and the spacing between the limit switches 28 and 29, a selective number of times, e.g. as counted by the counter 49, under selective tension as measured by the tensiometer 36. This simulates substantially actual field condition dragging as normally encountered by the cable in use.

The cable dragging longevity can thereby be determined by visual inspection of the cable exterior, including the condition of any exterior jacket as well as its interior mechanical and electrical integrity, either by taking the cable apart for inspection or by subjecting it to electrical conductivity or continuity tests, or the like, in conventional manner.

The loop test, in the first case, entails reciprocally moving only the second clutch drive 12, and specifically the reel 17 thereof, while the first clutch drive 11 remains stationary or inoperative, after having first preliminarily operated the first clutch drive 11 and the second clutch drive 12 to move via the reels 17 the forward end portion 9 of the test span 7 relative to the guide tube 6 and from the second reference point 4 to the first reference point 3 as accomplished in the forward movement cycle of the drag test.

Thus, in operating only the second clutch drive 12 and specifically the reel 17 thereof in a forward releasing feeding phase of reciprocal movement for corresponding movement of the rearward end portion 10 of the cable 8 from the guide tube 6, i.e. an outward further linear distance B corresponding to the circumference of the loop 7a to be formed and the spacing between the limit switches 29 and 30, the workman can form the loop on the drag surface area 7.

The loop 7a may be formed randomly anywhere along the test span 7 between the first reference point 3 and the second reference point 4, or by suitably marking one point on the intermediate section of the cable 8 in the drag test area 5, the loop 7a may be located at that specifically marked point each time. The workman can readily pull the cable outwardly from the guide tube 6 since the attachment line 23 is increasingly being fed out from the reel 17 of the second clutch drive 12 during this time, whereupon the loop 7a may be formed and properly sized as the bolt 25 on the collar 24 reaches the limit switch 30.

When the limit switch 30 is tripped, the second clutch drive 12 and specifically the reel 17 executes a rearward selective tension pulling return phase of reciprocal movement for a corresponding movement of the rearward end portion 10 of the cable 8 back into the guide tube 6 until the limit switch 29 is tripped. This causes the loop 7a to be removed under the resultant tension as the cable 8 becomes taut in reaching the rearward end of its loop forming and removing path. The tension on the cable 8 at this point may be readily measured by the tensiometer 36.

This cyclic unlooping procedure is repeated a selective number of times, e.g. as counted by the counter 48, and simulates substantially actual field condition looping and unlooping as normally encountered by the cable in use. The test may either be performed with or without relative rotational movement between the so looped cable and the guide tube 6 for correspondingly either relieving or propagating the tortional twisting inherently generated as the loop is removed, as earlier discussed.

The cable looping and unlooping longevity can thereby be determined by visual inspection of the cable exterior as in the drag test, since the looped cable is unlooped while at remains as a dead weight in contact with the drag surface area 5, as well as by taking the cable apart for inspection or by subjecting it to electrical conductivity or continuity tests, or the like, in conventional manner to ascertain its interior mechanical and electrical integrity.

The loop test, in the alternative second case, entails reciprocally moving only the first clutch drive 11 and specifically the reel 17 thereof while the second clutch drive 12 remains stationary or inoperative, likewise after having first preliminarily operated the first clutch drive 11 and the second clutch 12 to move via the reels 17 the forward end portion 9 of the test span 7 relative to the guide tube 6 and from the second reference point 4 to the first reference point 3 as accomplished in the forward movement cycle of the drag test.

Thus, in operating only the first clutch drive 11 and specifically the reel 17 thereof in a counterpart forward releasing feeding phase of reciprocal movement for corresponding movement of the forward end portion 9 of the cable 8 in a direction toward the second reference point 4 and the guide tube 6, i.e., a linear distance B corresponding to the circumference of the loop 7a to be formed and without regard to the limit switch 30 which may be omitted in this instance, the workman can form the loop on the drag surface area 5.

The loop 7a may be formed randomly anywhere along the test span 7 between the first reference point 3 and the second reference point 4, or by suitably marking off a length of the intermediate section of the cable 8 in the drag surface area 5 corresponding to the circumference of the loop 7a to be formed, the same may be located at that specifically marked location each time. The workman can readily pull the cable as fed via the reel 17 and attachment line 20 during this feeding time, whereupon the loop 7a may be formed and properly sized, and then the workman can signal the operator at the control console 40 to stop and reverse the operation of the reel 17, for any necessary adjustment in the loop size as and if needed and in turn to remove the loop.

The remainder of the second case loop test procedure is otherwise the same as that of the first case loop test, with appropriate measurement of the ultimate tension on the thusly unlooped cable, by the tensiometer 36, and with appropriate counting, e.g. by the counter 48, of the repeated cyclic unlooping operation for the number of times selected, and also with or without relative rotational movement between the so looped cable and the guide tube 6. The cable looping and unlooping longevity can be determined thereafter in the same way as in the first case loop test.

Optionally, expediently, a hand held push button remote control (not shown) operatively connected to the control console 40 may be used by the workman directly in the drag surface area 5 to control and/or adjust the feed of the attachment line 20 to facilitate formation of the loop 7a with the desired circumference, and in turn the reversal of the operation for removal of the loop. In this event, one person may serve both as the workman for forming the loop in the loop test and as the operator at the control console 40 for all other purposes.

The loop test, in the alternative third case, entails reciprocally moving both the first clutch drive 11 and the second clutch drive 12 and specifically the reels 17 thereof but in functionally opposite directions, similarly after having first premilinarily operated the two clutch drives concordantly to move via their reels 17 the forward end portion 9 of the test span 7 relative to the guide tube 6 and from the second reference point 4 to the first reference point 3 as accomplished in the forward movement cycle of the drag test.

Thus, in operating both the first clutch drive 11 and the second clutch drive 12 and specifically their reels 17 in functionally opposite directions for concordant counterpart forward releasing feeding phase dual reciprocal movement for corresponding movement of the forward end portion 9 of the cable 8 in a direction toward the second reference point 4 and the guide tube 6 and of the rearward end portion 10 of the cable in a direction toward the first reference point 3 and outwardly from the guide tube 6, i.e. an overall linear distance B corresponding to the circumference of the loop 7a to be formed and without regard to the limit switch 30 which may be omitted in this instance also, the workman as before can form the loop on the drag surface area 5.

The loop 7a similarly may be formed randomly anywhere along the test span 7 between the first reference point 3 and the second reference point 4, or by suitably marking of a length of the intermediate section of the cable 8 in the drag surface area 5 corresponding to the circumference of the loop to be formed, the same may be located at that specifically marked location each time. Likewise, the workman can readily pull the cable as jointly fed via both reels 17 and both attachment lines 20 and 23 during this feeding time to form and properly size the loop, and then signal the operator at the control console 40 to stop and reverse the operation of one or both reels 17 for any adjustment and finally for their dual reverse operation in functionally opposite directions to remove the loop.

On the other hand, the workman may use optionally said hand held push button remote control (not shown), also optionally usable in the second case loop test, as noted above.

The remainder of the third case loop test procedure is otherwise the same as that of the first case and second case loop tests, with appropriate measurement by the tensiometer 36 of the ultimate dynamic bidirectional pulling tension on the thusly unlooped cable generated by the oppositely pulling attachment lines 20 and 23 under the corresponding torques of the reels 17, and with appropriate counting, e.g. by counter 48 or otherwise, of the repeated cycle unlooping operation for the number of times selected, and also with or without relative rotational movement between the so looped cable and the guide tube 6. The cable looping and unlooping longevity can be determined thereafter in the same way as in the first case and second case loop tests.

The flex test entails operatively mounting the test span 7 of the cable 8 on a series of at least two tandem pulleys 32 and 33 having corresponding spaced apart, and preferably substantially parallel, axes of rotation 34 and 35 for tandem alternate reverse directional or sinuous path flexing of the test span 7 during movement in each reciprocal direction therethrough, and reciprocally moving simultaneously, e.g. concordantly synchronously, at selective speed the first clutch drive 11 and the second clutch drive 12, and specifically the reels 17 thereof, so as to move the test span 7 relative to the guide tube 6 and back and forth in the region encompassed between the first reference point 3 and the second reference point 4, i.e. at a movement amplitude corresponding to the linear distance C and the spacing between the limit switches 31 and 29, and through the tandem pulleys 32 and 33, under tandem alternate reverse directional or sinuous path flexing in each reciprocal direction of movement through the pulleys, a selective number of times, e.g. as counted by the counter 49, under selective tension as measured by the tensionmeter 36.

The cable flexing longevity can thereby be determined by visible inspection of the cable exterior, including the condition of any exterior jacket as well as its interior mechanical and electricaly integrity, either by taking the cable apart for inspection or by subjecting it to electrical conductivity or continuity tests, or the like, in conventional manner.

Where the cable has previously been subjected to the drag test, or is otherwise under selective slack tension at least in one reciprocal direction of phase movement permitting or resulting in the cable being dragged back and forth on a portion of the drag surface area 5 thereat during the flex test itself, that dragged cable will contain adhering to its outer jacket or surface a normal amount of the dirt or ground formation, e.g. sand particles, picked up from the drag surface area 5 during dragging contact therewith. Hence, as the cable passes back and forth through the tandem pulleys, the dirt, e.g. sand particles, adhering to the cable outer jacket or surface will cause abrasion to occur thereat in the same way as such abrasion occurs under service conditions when the cable after having been dragged along the ground is then passed through one or more guide pulleys under tension.

This dirt adhering modified type flex test will thus simulate substantially actual field condition flexing, and in a more intensive manner where a series of at least two tandem pulleys are provided, enabling the cable outer jacket or surface longevity with regard to pulley abrasion to be determined in a rapid and essentially valid as well as reliable manner.

Since the cable outer jacket or surface in this back and forth reciprocating sinuous path flex test, will be flexed first to the right and then to the left in one direction of movement between the reference points 3 and 4 and in turn will be flexed again first to the right and then to the left in the opposite direction of movement between the reference points 3 and 4, i.e. in the general manner in which such cable is flexed in practice, the longevity and structural integrity of such outer jacket or surface can be correspondingly readily effectively tested for and determined by this type of flex test, whether any dirt, e.g. sand particles, are present adhering thereto or not.

Moreover, in an alternative dirt adhering modified type flex test, by placing slight slack in the test span 7 as mounted on the pulleys with respect to each of the attachment lines 20 and 23, the actual portion of the cable 8 being tested may drag along the drag surface area 5 on each side of the two pulleys during the back and forth movement, i.e. in the same manner as in the drag test, so that the outer jacket of the cable will contain such dirt, e.g. sand particles, adhering thereto during passage through the pulleys, whereby to test the cable under more vigorous conditions.

It will be seen that the cable test arrangement 1 may be transformed from one test layout to the next with little effort by simply mounting or demounting the cable relative to the pulleys 32 and 33, and compensatingly adjusting the hook 21 at the forward end portion 9 of the cable 8, with respect to the flex test, and by simply moving the collar 24 and cable 8 from the range corresponding to the distance B and the positions of the limit switches 30 and 29, with respect to the loop test, to the range corresponding to the distance A and the positions of the limit switches 29 and 28, with respect to the drag test. Since the range of the flex test lies generally within that of the drag test, the only adjustment as between these two tests, i.e. other than with regard to the cable mounting on and demounting from the pulleys and compensating hook adjustment, will be the selection of the particular pair of limit switches.

It will be realized, of course, that the operator may select the timing of the switching into and out of operation of the reels 17 in each individual direction of movement, in the drag test and flex test, to adjust the degree of line tension placed on the cable 8 between the concordantly moving first attachment line 20 and second attachment line 23. This may also be accomplished by applying a selective braking action in conventional manner to the reel 17 which in that phase of movement is feeding out its attachment line. In either event, there will be a differential in the peripheral speeds of concordant rotation of the opposed reels 17, with the takeup reel acting as a torque drive to the selective extent corresponding to the selective tension to be applied to the cable.

Such selective tension is readily measured by the tensiometer 36 on the attachment line 20, especially in the forward movement phase in the direction from the second reference point 4 to the first reference point 3 of the drag test and the flex test.

As to the loop test, the cable is only subjected to tension at the end of the rearward pulling phase in removing the loop 7a.

In the first case loop test, since the first clutch drive 11 and its reel 17 and attachment line 20 are stationary during the test, the tension measured by the tensiometer 36 will increase to a maximum upon complete removal of the loop as the collar 24 and the rearward end portion 10 of the cable approach and finally reach the position of the limit switch 31. Here, the maximum tension applied to the cable is directly dependent upon the torque of the reel 17 of the second clutch drive 12 at the moment the collar 24 and the rearward end portion 10 of the cable reach the limit switch 31.

In the second case loop test, since the second clutch drive 12 and its reel 17 and attachment line 23 are stationary during the test, the tension measured by the tensiometer 36 will increase to a maximum upon complete removal of the loop whereupon the tension on the unlooped cable will be directly dependent upon the torque of the reel 17 of the first clutch drive 11. This can be standardized by providing a selectively adjustable conventional slip friction clutch in the clutch system 15 thereof to control the maximum tension exerted on the thusly unlooped cable.

In the third case loop test, since both clutch drives are used, the maximum tension measured by the tensiometer 36 upon complete removal of the loop will be directly dependent on the bilateral or bidirectional resultant force of the opposing torques of the oppositely pulling reels 17. Such can be standardized by providing a selectively adjustable conventional slip friction clutch in one or both of the clutch systems 15 in the same manner as in the second case loop test.

It will be appreciated that the foregoing specification and drawings are set forth by way of illustration and not limitation, and that various modifications and changes may be made therein without departing from the spirit and scope of the present invention which is to be limited solely by the scope of the appended claims.

What is claimed is:

1. Cable tester arrangement for subjecting cable such as mining cable to simulated field conditions substantially corresponding to actual field conditions as normally encountered by the cable for determining cable longevity, comprising
   a support surface having a first reference point and a second reference point spaced apart a selective distance and defining a test drag surface area therebetween,
   a source means adjacent the second point for feed and return of a selective length of a test span of such a cable having a forward cable end portion and a rearward cable end portion,
   first selectively operatable moving means operatively connectable to the cable for moving the forward end portion of the test span of the cable from the second point to the first point, and second selectively operatable moving means operatively connectable to the cable for moving the rearward end portion of the test span of the cable from the second point to the source means, and
   control means arranged for selectively independently controlling the operation and movement of the first moving means and second moving means,
   for operation in a first test mode for simultaneous reciprocal movement of the first moving means and second moving means to move the test span of the cable relative to the source means and drag the test span back and forth along the drag surface area between the first point and the second point a selective number of times under selective tension to simulate substantially actual field condition dragging as normally encountered by the cable for determining cable dragging longevity, and
   alternatively for operation in a second test mode for reciprocal movement of at least one said moving means relative to the other said moving means to permit the forming of a selectively sized loop in an intermediate section of the test span of the cable on the drag surface area between the first point and the second point in a forward releasing feed phase of reciprocal movement of said at least one moving means, and then the removing of the loop in a rearward selective tension pulling return phase of reciprocal movement of said at least one moving means, a selective number of times to simulate substantially actual field condition looping and unlooping as normally encountered by the cable for determining cable looping and unlooping longevity.

2. Arrangement according to claim 1 wherein cable tension measuring means are provided for measuring the tension of the test span of the cable.

3. Arrangement according to claim 1 wherein the source includes an elongated cable receiving guide.

4. Arrangement according to claim 3 wherein the guide is interposed between the second moving means and the second point.

5. Arrangement according to claim 4 wherein the first moving means and the second moving means each respectively includes an attachment line connectable to the cable and arranged for feed from and take up onto a reciprocally rotatable reel controlled by the control means.

6. Arrangement according to claim 5 wherein cable tension measuring means are provided operatively on the attachment line of the first moving means for measuring the tension of the test span of the cable.

7. Arrangement according to claim 5 wherein the control means includes cam operated linear limit actuation means selectively disposed in the guide, and the attachment line of the second moving means is provided with cooperating cam means and is arranged for movement along the guide to permit the cam means to operate the limit actuation means for correspondingly controlling the operation of the moving means.

8. Arrangement according to claim 1 wherein the first moving means and second moving means are electrically controlled, and the control means includes an energizable circuit for electrically independently controlling the first moving means and the second moving means and contains selectively arranged limit switch means correspondingly actuated in dependence upon the movement amplitude selected between the first reference point and the second reference point.

9. Arrangement according to claim 1 wherein cable flexing pulley means are provided adjacent the drag surface area and disposed between the first point and second point, and the control means is arranged for selectively controlling the operation and movement of the first moving means and second moving means for operation in a third test mode for simultaneous reciprocal movement of the first moving means and second moving means to move the test span of the cable, operatively mounted on the pulley means, relative to the source means and flexibly back and forth through the pulley means a selective number of times under selective tension for determining cable flexing longevity.

10. Arrangement according to claim 9 wherein the pulley means includes a series of at least two tandem pulleys having corresponding spaced apart axes of rotation for tandem alternate reverse directional flexing of the test span of the cable during movement in each reciprocal direction therethrough.

11. Method of using a cable tester arrangement according to claim 10 for carrying out an alternate reverse directional flex test with a test span of cable having a forward end portion and a rearward end portion, comprising
    operatively connecting the first moving means to the forward end portion of the test span of the cable and the second moving means to the rearward end portion of the test span of the cable, and operatively mounting the test span of the cable on the tandem pulleys, and
    reciprocally moving simultaneously the first moving means and second moving means to move the test span of the cable relative to the source means and flexibly back and forth through the tandem pulleys, under tandem alternate reverse directional flexing in each reciprocal direction of movement through the pulleys, a selective number of times under selective tension for determining alternate reverse directional cable flexing longevity.

12. Method of using a cable tester arrangement according to claim 1 for carrying out a drag test with a test span of cable having a forward end portion and a rearward end portion, comprising operatively connecting the first moving means to the forward end portion of the test span of the cable and the second moding means to the rearward end portion of the test span of the cable, and reciprocally moving simultaneously the first moving means and second moving means to move the test span of the cable relative to the source means and drag the test span back and forth along the drag surface area between the first point and the second point a selective number of times under selective tension to simulate substantially actual field condition dragging as normally encountered by the cable for determining cable dragging longevity.

13. Method of using a cable tester arrangement according to claim 1 for carrying out a loop test with a test span of cable having a forward end portion and a rearward end portion, comprising operatively connecting the first moving means to the forward end portion of the test span of the cable and the second moving means to the rearward end portion of the test span of the cable, and reciprocally moving at least one said moving means relative to the other said moving means and correspondingly forming a selectively sized loop in an intermediate section of the test span of the cable on the drag surface area between the first point and the second point in a forward releasing feed phase of reciprocal movement of said at least one moving means and a corresponding forward feed phase movement of the cable, and then correspondingly removing the loop in a rearward selective tension pulling return phase of reciprocal movement of said at least one moving means and a corresponding rearward return phase movement of the cable, a selective number of time to simulate substantially actual field condition looping and unlooping as normally encountered by the cable for determining cable looping and unlooping longevity.

* * * * *